United States Patent [19]

WoldeMussie et al.

[11] Patent Number: 5,521,210
[45] Date of Patent: May 28, 1996

[54] OPHTHALMIC USE OF MUSCARINIC AGONISTS HAVING INCREASED DURATION OF ACTIVITY

[75] Inventors: Elizabeth WoldeMussie, Laguna Niguel, Calif.; Roger F. Steinert, North Andover, Mass.; Guadalupe Ruiz, Corona, Calif.

[73] Assignee: Allergan, Inc., Irvine, Calif.

[21] Appl. No.: 48,829

[22] Filed: Apr. 13, 1993

[51] Int. Cl.$^6$ .................................................. A61K 31/40
[52] U.S. Cl. .......................... 514/424; 514/408; 514/422; 514/912; 514/913
[58] Field of Search ................................. 514/424, 912, 514/913, 422, 408; 548/524

[56] References Cited

U.S. PATENT DOCUMENTS

| | | | |
|---|---|---|---|
| 3,444,185 | 5/1969 | Pierre et al. | 260/326.3 |
| 3,450,814 | 6/1969 | Bechtold et al. | 424/180 |
| 3,608,073 | 9/1971 | Kaspar et al. | 424/168 |
| 3,824,313 | 7/1974 | Smythies | 424/274 |
| 3,920,824 | 11/1975 | Rajadhyaksha | 424/274 |
| 3,947,573 | 3/1976 | Rankin | 424/80 |
| 3,978,201 | 8/1976 | Khromou et al. | 424/7 |
| 4,003,991 | 1/1977 | Krohn et al. | 424/81 |
| 4,136,178 | 1/1979 | Lin et al. | 424/211 |
| 4,407,792 | 10/1983 | Schoenwald et al. | 424/81 |
| 4,597,965 | 7/1986 | Holly | 424/81 |
| 4,668,506 | 5/1987 | Bawa | 424/429 |
| 4,742,073 | 5/1988 | Bundgaard et al. | 514/400 |

OTHER PUBLICATIONS

Investigative Ophthalmology vol. 14, No. 3 1975 pp. 232–235.
Archives of Pharmacology vol. 338, No. 5, 1988 pp. 476–483.
Journal of Medicinal Chemistry vol. 31, No. 3, 1988 pp. 683–688.
Exp. Eye Res. vol. 56, No. 4, Apr. 1, 1993, pp. 385–392.
The Japanese Journal of Pharmacology vol. 38 No. 1, 1985.

*Primary Examiner*—Shailendra Kumar
*Attorney, Agent, or Firm*—Walter A. Hackler

[57] ABSTRACT

A method for inducing prolonged pseudoaccommodation includes the instillation of an ophthalmic formulation into an eye for contracting the iris sphincter muscle, but not the ciliary muscle, in order to cause sphincter muscle contraction for a period of greater than about one hour per instillation. The method further provides for the stabilization of an implanted intraocular lens immediately after surgery and for reducing glare following radial keratotomy.

1 Claim, 2 Drawing Sheets

OPHTHALMIC USE OF MUSCARINIC AGONISTS HAVING INCREASED DURATION OF ACTIVITY

The present invention generally relates to ophthalmic use of muscarinic agonists and specifically is directed to muscarinic agonists having increased duration of activity for long periods of time.

Contraction of the pupil due to constriction of the iris sphincter by topically applied agents may be desirable in a great number of situations.

For example, stabilization of an implanted intraocular lens immediately after surgery is facilitated by the use of an ophthalmic formulation which causes constriction of the iris sphincter. Also, suitable accommodation, particularly for persons having intraocular lenses, may be obtained by maintaining a small pupil diameter, in that a constricted pupil provides a small aperture which results in "pseudoaccommodation" by increasing the depth of field.

In addition, many pseudophakic patients have light phobia because of the extreme clarity of the intraocular lens. In this case, reduction in the pupillary sizes is advantageous.

As a further application, there is a potential significant application in refractive surgery. Radial keratotomy (RK) is the incisional technique to reduce myopia. Excimer laser photorefractive keratectomy (PRK) utilizes the laser energy to reshape the center of the cornea, typically with an optical zone of 5 mm to 6 mm. For both of these procedures, a frequent complaint in the first six postoperative months is that of glare at night. In the case of RK, the glare typically is a "starburst" pattern from directed light sources such as headlights and streetlights; in PRK the most typical description is that of a halo-type of circular glare around the directed light sources. In both cases, the problem is principally due to the natural dilation of the pupils at night, so that light enters the pupil after first encountering the radial scars of RK or the edge of the circular treatment zone in PRK.

Miotic drops could offer these patients considerable relief from the glare symptoms by preventing the excessive dilation at night. A problem with the current miotic drops such as Pilocarpine is that they also cause contraction of the ciliary muscle which induces a considerable amount of myopia in most young phakic patients undergoing refractive surgery. A miotic drop that does not also induce myopia would be of considerable benefit.

Many parasympathomimetic preparations are available for intraocular use for causing rapid myosis, such as acetylcholine chloride or Miochol®. This miotic is a naturally occurring neuro hormone which mediates nerve impulse transmission at cholinergic sites involving somatic and autonomic nerves.

This ophthalmic formulation is in general use for obtaining miosis of the iris in seconds after delivery of the lens in cataract surgery, in penetrating keratoplasty, iridectomy and other interior segment surgery where rapid, complete miosis may be required.

Unfortunately, the activity of acetylcholine chloride is of short duration. Therefore, in combination, pilocarpine may be topically applied to sustain miosis. Pilocarpine, or pilocarpine monohydrochloride, is typically used as an ophthalmic cholinergic. However, a serious problem associated with pilocarpine is its short duration of action. In addition, ciliary spasm may occur. In addition to ciliary spasm, other adverse reactions to pilocarpine include conjunctival vascular congestion, temporal or supraorbital headache, and lacrimation.

SUMMARY OF THE INVENTION

A method in accordance with the present invention for inducing prolonged pseudoaccommodation includes the instillation of an ophthalmic formulation into an eye for contracting the iris sphincter muscle, but not the ciliary muscle, in order to cause sphincter muscle contraction for a period greater than about one hour per instillation. More particularly, the ophthalmic formulation in accordance with the method of this invention will comprise a muscarinic agonist having a duration of activity of greater than one hour per instillation. A sufficient fluid amount of ophthalmic formulation may be instilled in order to cause pupil reductions of more than 75% for twelve hours or more. This is an important feature of the present invention and enables the treatment for glare and "starburst" following radial keratotomy or excimer laser photorefractive keratotomy as well as providing a means for holding and supporting a newly inserted intraocular lens following cataractic surgery.

More particularly, the method in accordance with the present invention includes the step of instilling an ophthalmic formulation comprising, in an amount effective to constrict the iris sphincter muscle for a period of greater than one hour, a compound represented by the general formula:

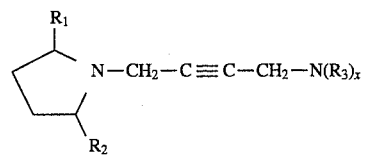

wherein $R_1$ represents two hydryl (H) radicals or an oxo (O) radical, $R_2$ represents two hydryl (H) radicals or a lower alkyl radical having up to 4 carbon atoms, $R_3$ represents a lower alkyl radical having up to 4 carbon atoms and x is an integer of from 1 to 3, with the proviso that when x is 1, $R_3$ and N, together, form a cycloamino radical comprising a 3- to 5-member ring and when x is 3, the muscarinic agent is a quaternary salt.

More specifically, the method in accordance with the present invention includes the instillation of a formulation comprising at least about 0.5% of one of the above compounds.

More preferably, the formulation may comprise between about 0.5% and about 2% of one of the above compounds. Most preferably the compound is N-(4-azetidinyl-2-butynyl)-5-methyl-2-pyrrolidone.

In accordance with the present invention, a muscarine agonist comprising N-(4-azetidinyl-2-butynyl)-5-methyl-2-pyrrolidone may be instilled in order to reduce pupil diameter for periods of up to 24 hours or more.

Further, in combination, the method of the present invention includes the steps of performing ophthalmic surgery on an eye and thereafter instilling into the eye an ophthalmic formulation for contracting the iris sphincter muscle but not the ciliary muscle in order to cause sphincter muscle contraction for a period of greater than about one hour per instillation.

More specifically, the method may include surgically removing a cataractus crystalline lens from a patient's eye, replacing the removed cataractus crystalline lens with an intraocular lens, and providing instruction to the patient to instill an ophthalmic formulation into the intraocular lens replaced eye at a frequency corresponding to an activity of the formulation for causing iris sphincter contraction with the period being greater than one hour.

BRIEF DESCRIPTION OF THE DRAWINGS

The advantages and features of the present invention will be better understood by the following description when

DETAILED DESCRIPTION

Figure 1:
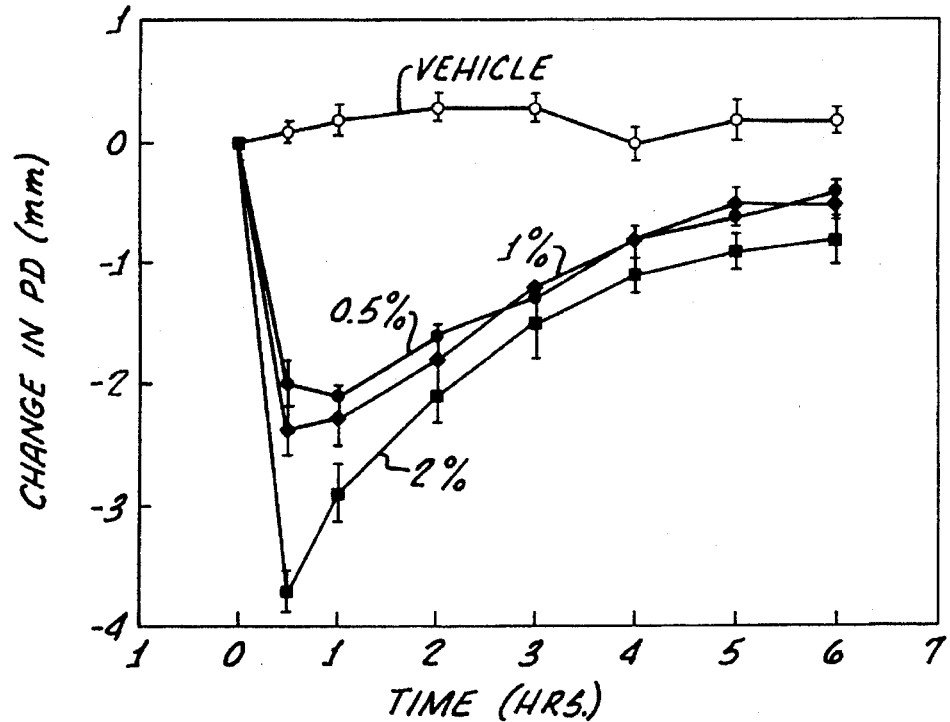
FIG. 1 is a plot of a change in pupil diameter in rabbits as a function of time caused by the instillation of formulations in accordance with the present invention.

Suitable formulations for use in the present invention include the formulations comprising

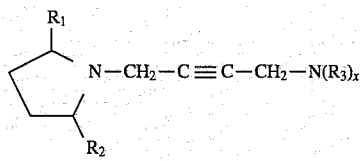

wherein $R_1$ represents two hydryl (H) radicals or an oxo (O) radical, $R_2$ represents two hydryl (H) radicals or a lower alkyl radical having up to 4 carbon atoms, $R_3$ represents a lower alkyl radical having up to 4 carbon atoms and x is an integer of from 1 to 3, with the proviso that when x is 1, $R_3$ and N, together, form a cycloamino radical comprising a 3- to 5-member ring and when x is 3, the muscarinic agent is a quaternary salt.

Preferably, the formulation in accordance with the present invention is N-(4-azetidinyl-2-butynyl)-5-methyl-2-pyrrolidone.

The N-(4-azetidinyl-2-butynyl)-5-methyl-2-pyrrolidone is an analog of oxotremorine and may be prepared in accordance with the process set forth in U.S. Pat. No. 3,444,185.

The applicants have discovered unexpected activity of the muscarinic agonist N-(4-azetidinyl-2-butynyl)-5-methyl-2-pyrrolidone in causing selective contraction of the iris sphincter muscle with little effect on the ciliary muscle. This is to be distinguished from current miotic drops, such as pilocarpine, which cause contraction of the ciliary muscle, which thereby induces a considerable amount of myopia.

Not only is the specific activity limited to the iris sphincter muscle but the duration of its effect is significantly longer than that of pilocarpine, as evidenced by the hereinafter set forth examples, which include testing in rabbits, owl monkeys, and the cynomolgus monkeys.

Any pharmaceutically appropriate inert vehicle or carrier system for the ophthalmic instillation, or administration, of the formulation in accordance with the present invention, which are well-known to those skilled in the art of ophthalmic pharmaceutical formulations, may be utilized. Thus, pharmaceutically acceptable carriers for the preparation of eye drops for a conventional or common vehicle buffer system include isotonic boric acid, or boric solutions, isotonic saline vehicles, and the like, with or without polymers and/or viscosity altering additives, such as hydroxypropyl cellulose, methyl cellulose, polyvinyl polyvinylpyrrolidone, polyvinyl alcohol, or polyacrylamide.

The formulation in accordance with the present invention may be administered as a single dose, a daily dose, or other time-presented dose regimes, depending upon the requirement of the individual under treatment. The dose which is to be administered is, therefore, not subject to any specific limits, despite the dosage set forth in the following examples.

EXAMPLES

The following examples recording the effect of duration of the activity of N-(4-azetidinyl-2-butynyl)-5-methyl-2-pyrrolidone on pupil diameter are representative in showing the constriction of the iris sphincter and, no ciliary spasm was observed.

In these studies, owl monkeys, cynomolgus monkeys, and New Zealand—Cross-Dutch Belted (NZ X DD) rabbits were used. The N-(4-azetidinyl-2-butynyl)-5-methyl-2-pyrrolidone solution in amounts of about 0.5% to about 2.0% were topically applied into one eye of the owl monkeys, cynomolgus monkeys and rabbits. The other eye was left untreated and control animals received a saline vehicle. The pupil diameter (PD) was measured with an Optistick® ruler every one or two hours from time zero to six hours. The results shown are mean±S.E. of three or more animals.

The results of the instillation of 25 microliter formulation in rabbit eyes is shown in FIG. 1. As can be seen, the N-(4-azetidinyl-2-butynyl)-5-methyl-2-pyrrolidone caused a dose-related decrease in the pupil diameter with a maximum response after thirty minutes. Each point represents the mean±S.E. of six, animals where the pupil diameter at time zero of 6.5±0.2 mm. The immediate onset of pupil restriction is evident on the plot as well as the duration of pupil restriction.

Figure 2:
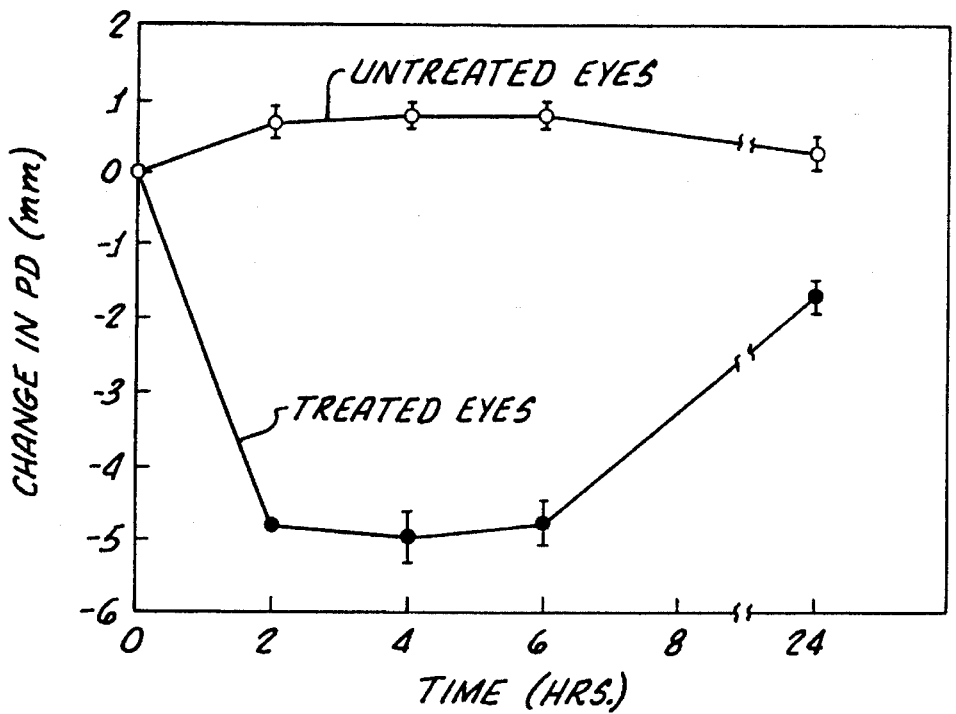
FIG. 2 is a plot of the change in pupil diameter for owl monkeys as a function of time as a result of instillation in accordance with the present invention.

In FIG. 2, the effect of a 0.5% N-(4-azetidinyl-2-butynyl)-5-methyl-2-pyrrolidone formulation on the pupil diameter of owl monkeys is shown for a 10 microliter instillation. It can be seen that the N-(4-azetidinyl-2-butynyl)-5-methyl-2-pyrrolidone caused a decrease of 92%–97% of pupil diameter for a period of between two and six hours after application. A decrease of 30% was still present after twenty-four hours (the pupil diameter at time zero was 5.2±0.4 mm.

Figure 3:
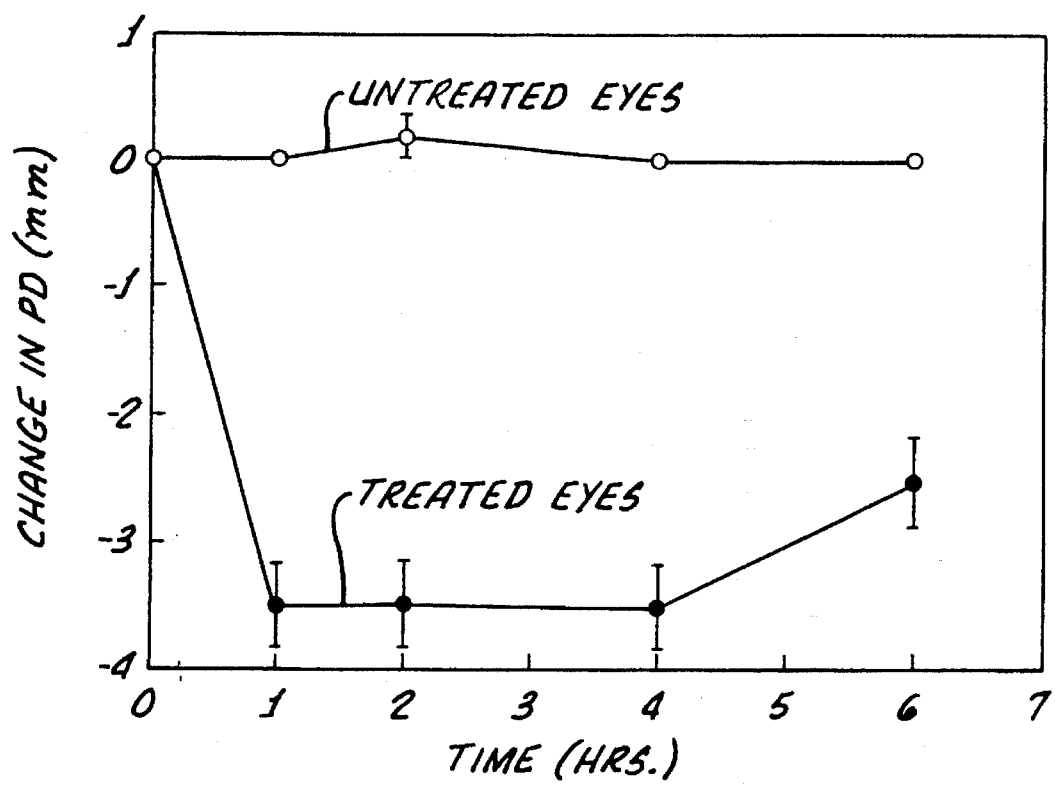
FIG. 3 is a plot of the change in pupil diameter of cynomolgus monkeys as a function of time in response to the instillation of formulations in accordance with the present invention.

FIG. 3 shows the effect of 25 microliter instillation of 1% formulation of N-(4-azetidinyl-2-butynyl)-5-methyl-2-pyrrolidone on the pupil diameter of cynomolgus monkeys. It can be seen that the N-(4-azetidinyl-2-butynyl)-5-methyl-2-pyrrolidone causes 75% decrease in pupil diameter for one to four hours after application, followed by partial recovery (pupil diameter at time zero was 4.6±0.2 mm.

Although there has been hereinabove described an ophthalmic use of muscarinic agonists in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A post-cataract surgery method comprising the step of instilling of an ophthalmic formulation into an eye for contraction of the iris sphincter muscle for a period of time greater than about one hour in order to hold an intraocular lens in place, said ophthalmic formulation comprising:

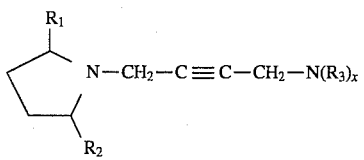
wherein $R_1$ represents two hydryl (H) radicals or an oxo (O) radical, $R_2$ represents two hydryl (H) radicals or a lower alkyl radical having up to 4 carbon atoms, $R_3$ represents a lower alkyl radical having up to 4 carbon atoms and x is an integer of from 2 to 3 and when x is 3, the muscarinic agent is a quaternary salt.
* * * * *